US012551673B2

(12) United States Patent
Bain

(10) Patent No.: US 12,551,673 B2
(45) **Date of Patent: *Feb. 17, 2026**

(54) SYSTEMS AND METHODS FOR IMPROVED ENHANCED DILATION DEVICES FOR TARGETED DILATATION DIAGNOSTICS AND THERAPIES

(71) Applicant: Growth Armor, LLC, Wilmington, DE (US)

(72) Inventor: Michael A. Bain, Costa Mesa, CA (US)

(73) Assignee: Growth Armor, LLC, Wilmington, DE (US)

( * ) Notice: Subject to any disclaimer, the term of this patent is extended or adjusted under 35 U.S.C. 154(b) by 317 days.

This patent is subject to a terminal disclaimer.

(21) Appl. No.: 18/186,820

(22) Filed: Mar. 20, 2023

(65) Prior Publication Data

US 2024/0316321 A1 Sep. 26, 2024

(51) Int. Cl.
*A61M 29/02* (2006.01)

(52) U.S. Cl.
CPC ....... *A61M 29/02* (2013.01); *A61M 2029/025* (2013.01); *A61M 2205/3344* (2013.01)

(58) Field of Classification Search
CPC ........ A61B 17/3468; A61B 2017/3427; A61B 5/036; A61N 1/0558; A61M 2025/0024; A61M 2025/0025; A61M 2025/0039; A61M 2025/0037; A61M 25/0026; A61M 25/0028; A61M 29/02; A61M 2205/8206; A61M 2205/8237; A61M 2210/1067; A61M 2210/1475; A61H 19/44;
(Continued)

(56) References Cited

U.S. PATENT DOCUMENTS

2005/0055043 A1 3/2005 Foltz et al.
2008/0188709 A1* 8/2008 Gil .................... A61H 23/0263 600/38
(Continued)

FOREIGN PATENT DOCUMENTS

CN 109512444 3/2019

OTHER PUBLICATIONS

PCT Search Report for PCT/US2024/020396; Sep. 26, 2024.

*Primary Examiner* — Jocelin C Tanner
(74) *Attorney, Agent, or Firm* — Stetina Garred Brucker & Newboles

(57) ABSTRACT

Systems and methods for improved enhanced dilation devices for targeted diagnosis and targeted dilatation therapy is contemplated. The enhanced dilation device have a plurality of inflation lumens which expand and retract via a plurality of pumps operative to pump an inflation fluid into and out of the plurality of inflation lumens so as to contact against diagnostic regions of a patient's dilated orifice in order to derive diagnostic statuses for the multitude of regions of a patient's dilatated orifice, and an aggregate diagnostic profile and a treatment methodology therefrom. The diagnostic device may also comprise a scanner with emitters operative to emit energy towards diagnostic regions of the body cavity the diagnostic device may be inserted into and sensors operative to detect the effects of this energy to generate one or more regional diagnostic statuses characterizing the body cavity.

14 Claims, 6 Drawing Sheets

(58) Field of Classification Search
CPC .............. A61H 19/40; A61H 2023/002; A61H 2201/0103; A61H 2201/0107; A61H 2201/1238; A61H 2201/5071; A61H 2201/5084; A61H 2201/5097
USPC ............................................. 606/129; 601/46
See application file for complete search history.

(56) References Cited

U.S. PATENT DOCUMENTS

| | | | | |
|---|---|---|---|---|
| 2010/0145224 | A1 | 6/2010 | Lee et al. | |
| 2014/0088468 | A1* | 3/2014 | Murison | A61H 23/04 601/150 |
| 2023/0293863 | A1* | 9/2023 | Bain | A61H 19/44 |

* cited by examiner

SYSTEMS AND METHODS FOR IMPROVED ENHANCED DILATION DEVICES FOR TARGETED DILATATION DIAGNOSTICS AND THERAPIES

CROSS-REFERENCE TO RELATED APPLICATIONS

Not applicable

STATEMENT RE: FEDERALLY SPONSORED RESEARCH/DEVELOPMENT

Not applicable

BACKGROUND

1. Field of the Invention

The present application relates to the field of dilation devices for therapeutic, diagnostic, and recreational purposes. More specifically, the present application relates to superior enhanced dilation devices and methods of using such devices to achieve targeted dilatation diagnostics therapies.

2. Related Art

There are a number of reasons for which an individual may utilize a device configured for insertion into the vagina or anus. Medically, there are a number of disorders that involve the pelvic area, including of the bladder, vagina, pelvic floor muscle, rectum and cervix, for which insertion of devices for therapeutic treatment is a common method of treatment. Likewise, such devices are often used for sexual stimulation purposes. Notably, the disclosure of Applicant's prior filed U.S. patent application Ser. No. 17/655,761, entitled IMPROVED DILATATION DEVICE INCORPORATING INFLATABLE BALLOON, Applicant's prior filed U.S. patent application Ser. No. 17/646,309 entitled ENHANCED PROPHYLACTICS FOR VACUUM THERAPY, Applicant's prior filed U.S. patent application Ser. No. 17/809,357 entitled IMPROVED DILATATION DEVICES INCORPORATING ENHANCED FEATURES, and Applicant's prior filed U.S. patent application Ser. No. 17/931,411 entitled RESILIENT ADHESIVE SHEATH FOR USE WITH DILATION DEVICE are important to complete the understanding of the disclosure made herein, and accordingly, the entire disclosure of each is incorporated herein as if fully restated.

The pubococcygeal muscle, commonly called the pelvic floor muscle, is responsible for holding all the pelvic organs within the pelvic cavity. The pelvic floor muscle consists of a deep muscle layer and a superficial muscle layer that work together to keep the pelvic organs healthy and in good working order. The muscle is suspended at the base of the pelvis and wraps around the vagina and rectum. The pelvic floor muscles may become damaged or weakened through childbirth, lack of use, aging, illness, or as the collateral result of surgical procedures. One of the symptoms related to a weakening of these muscles is urinary incontinence.

Other pelvic disorders include chronic pelvic pain and vulvodynia (pelvic muscle dysfunction), which may sometimes be experienced by young adult women. These disorders may be caused by involuntary contractions (spasms) of the levator ani and perineal muscles. This condition, sometimes referred to as vaginismus or pelvic floor tension myalgia, may be accompanied by difficult and painful penetration of the vagina (dyspareunia), often resulting in pain and other difficulties which substantially reduce a woman's quality of life, not only with regard to the participating in and enjoyment of penetrative sexual intercourse, but also in other facts of life, such as in the use of menstrual products such as tampons or during routine procedures such as the use of speculums during gynecological examinations.

Dilatation devices are commonly prescribed for the treatment of such conditions, and generally include products such as vaginal dilators and Kegel exercisers. Similarly, dilatation devices for insertion into the anus may also be prescribed, for example, in order to aid in treatment of conditions such as anal stenosis, where treatment involves progressive stretching and acclimation of the rectum to an ideal size to improve comfort and function following anorectal procedures, such as following surgeries on the prostate or for hemorrhoids.

Similarly, dilatation devices are also used for the enhancement of sexual pleasure, and in this context, such devices generally are referred to as sex toys. There may also be substantial overlap between the structure and functionality of devices adapted for therapeutic and recreational uses, and in many cases, especially when a pelvic disorder may directly impact the ability to enjoy sexual intercourse and pleasure, a single device may be utilized for both purposes. Many types of sex toys are known. Some of the most popular sex toys are designed for vaginal or anal insertion, and include items such as dildos, prostate stimulators, anal plugs, etc. Many of these devices may also include other stimulatory elements, such as vibrating or rotating functionalities.

Conventional dilatation devices suffer from a number of deficiencies. For example, conventional treatment of vaginismus or anal stenosis typically entails the progressive insertion of a progressively larger sequence of dilators until the vagina or anus becomes acclimated to the desired size. It is therefore desirable to have improved dilatation devices which may, for example, provide adaptive forms of dilatation therapies, potentially even taking into consideration biofeedback mechanisms and measuring them in order administer the optimal therapeutic treatment to a user. Likewise, similar deficiencies may exist in the field of sex toys, and consequently, overall sexual pleasure may be enhanced the application of similar techniques to produce improved sex toys for insertion.

Accordingly, Applicant has developed certain innovations in the field of dilatation devices, which allow for adaptive forms of dilatation therapy using a single complex device, where prior methods of treatment may require the use of a number of devices.

BRIEF SUMMARY

To solve these and other problems, an enhanced dilatation device is contemplated in which technologies pioneered in catheterized balloon techniques such as angioplasty, and other enlargement or disocclusion procedures may be applied to conventional devices in novel ways. In particular, a tubular balloon may be positioned around the shaft of a conventional rigid dilatation device (e.g. vaginal or anal dilators, penetrative sex toys (dildos), pelvic floor/Kegel trainers and stimulators, etc.), with a reservoir inside the body of the dilatation device filled with an inflation fluid such as helium gas. Via the action of a pump which transfers the inflation fluid to and from the internal fluid reservoir along a plurality of inflation fluid pathways to a plurality of internal lumens within the balloon, which is formed of a resilient but flexible material, may be seen to inflate and deflate, resulting in enhanced and controllable dilatation beyond that provided by the insertion of the rigid dilatation device alone. Furthermore, it is contemplated that enhanced control mechanisms may enable the inflation and deflation of one or more balloon portions of the device by selectively controlling the inflation and deflation of the inflation lumens of the balloon. When inserted into the body cavity of a user, this effect can be taken advantage of to create diagnostic profiles characterizing the body cavity and to administer a treatment methodology specific to treat that diagnostic profile. A scanner unit may be incorporated into the enhanced dilation device, or used in a separate diagnostic device, to determine the diagnostic profiles that characterize the body cavity.

An enhanced dilation device for targeted dilation therapy may comprise a rigid elongated member having a proximal end, a distal end, and a shaft region therebetween, a sheath secured to and at least partially enclosing at least a portion of an exterior of the shaft region, with the sheath having an outer surface and a plurality of inflation lumens and each individual one of the plurality of inflation lumens being transitionable between at least a deflated configuration and an inflated configuration. The transitioning of each individual inflation lumen to the inflated configuration is operative to cause a respective inflation portion of the outer surface corresponding to that inflation lumen to expand away from the exterior of the shaft region, and the transitioning of each individual inflation lumen to the deflated configuration is operative to cause that respective inflation portion of the outer surface corresponding to that inflation lumen to retract towards the exterior of the shaft region.

An enhanced dilation device may further comprise a reservoir operative to contain inflation fluid, a plurality of conduits defining respective inflation fluid pathways between the reservoir and each respective inflation lumen, a plurality of pumps, with at least one pump being associated with each inflation fluid pathway and each at least one pump being operative to regulate the net flow of inflation fluid between the reservoir and a respective inflation lumen along the respective inflation fluid pathway. A net flow of inflation fluid from the reservoir into a respective inflation lumen is associated with the transition of that inflation lumen to the inflated configuration, and a net flow of inflation fluid from the respective inflation lumen into the reservoir is associated with the transition of that inflation lumen to the deflated configuration. The enhanced dilation device may further comprise a plurality of pressure sensors, with each respective one of the inflation lumens having associated therewith at least one respective pressure sensor for measuring the pressure within that inflation lumen. The enhanced dilation device may further comprise a control unit operative to control at least the operation of the plurality of pumps and to receive measurements from the plurality of pressure sensors.

An enhanced dilatation device may be operative to perform a diagnostic sequence for characterizing a patient's body cavity into which the rigid elongate member is inserted, the diagnostic sequence comprising one or more of the plurality of inflation lumens being transitioned to the inflated configuration such that each respective inflation portion of the outer surface corresponding to those one or more inflation lumens expands against a respective corresponding diagnostic region of the body cavity and each at least one pressure sensor associated with the one or more of the plurality of inflation lumens transitioned to the inflated configuration detects at least one pressure measurement within that inflation lumen. Based upon the at least one detected pressure measurement, a regional diagnostic status is determined for each diagnostic regions of the body cavity.

A regional diagnostic statuses may also be determined by a combination of the at least one detected pressure measurement and the net flow of inflation fluid flowed to the one or more of the plurality of inflation lumens via the operation of the pump associated with the inflation fluid pathway between the one or more plurality of inflation lumens and the reservoir. The regional diagnostic statuses may additionally be determined based upon a plurality of the detected pressure measurements taken at different times during the transitioning of that inflation lumen to the inflated configuration. Each of the determined diagnostic statuses for each diagnostic region of the body cavity may be utilized to generate an aggregate diagnostic profile corresponding to the body cavity.

Following the performance of any of the aforementioned diagnostic sequences, an enhanced dilatation device may be operative to administer treatment to the patient via the rigid elongate member remaining inserted or being re-inserted within the patient's body cavity in a substantially similar spatial orientation as in the diagnostic sequence, and the control unit being operative to control the operation of at least one of the pumps to perform a treatment methodology derived from at least the aggregate diagnostic profile corresponding to the body cavity. The treatment methodology may comprise the transitioning of at least one of the plurality of inflation lumens to the inflated configuration, such that targeted dilatation is delivered to at least one of the diagnostic regions of the patient's body cavity.

A treatment methodology may comprise one or more of the transitioning of a particular selected one or more of the inflation lumens to the inflated configuration, the transitioning of one or more inflation lumens to the inflated configuration so as to achieve a predefined particular measurement at the one or more pressure sensors associated with those inflation lumen, the transitioning of one or more inflation lumens between the inflated configuration and the deflated configuration a particular number of times over a particular time period, the transitioning of an inflation lumen to the inflated configuration or to the deflated configuration over a particular rate of time, or combinations thereof. Following the performance of one or more treatment methodologies, the enhanced dilatation device may be operative to repeat the performance of the diagnostic sequence in order to assess the results of the performance of the one or more treatment methodologies and to generate a new regional diagnostic status for each of the diagnostic regions of the body cavity. The repeat performance of the diagnostic sequence may be performed via the rigid elongate member remaining inserted or being re-inserted within the patient's body cavity in a substantially similar spatial orientation as in the previous diagnostic sequence.

A method for performing a diagnostic sequence for characterizing a patient's body cavity is also contemplated, and may comprise the steps of providing an enhanced dilation device according to the first exemplary enhanced dilation device described above, inserting the rigid elongate member into the patient's body cavity and causing one or more of the plurality of inflation lumens to be transitioned to the inflated configuration such that each respective inflation portion of the outer surface corresponding to those one or more inflation lumens expands against a respective corresponding diagnostic region of the body cavity and each at least one pressure sensor associated with the one or more of the plurality of inflation lumens transitioned to the inflated configuration detects at least one pressure measurement within that inflation lumen, and determining from the at least one detected pressure measurement, a regional diagnostic status for each diagnostic regions of the body cavity.

It is contemplated that at least one regional diagnostic status for at least one of the diagnostic regions of the body cavity may be determined based upon a combination of the at least one detected pressure measurement within the inflation lumens corresponding to that at least one diagnostic region, and the net flow of inflation fluid flowed to that inflation lumen via the operation of the pump associated with the inflation fluid pathway between that inflation lumen and the reservoir. Each regional diagnostic status for each of the respective diagnostic regions of the body cavity may be determined based upon a plurality of detected pressure measurements within the inflation lumens corresponding to that diagnostic region taken at different times during the transitioning of that inflation lumen to the inflated configuration. Each of the determined regional diagnostic statuses for each diagnostic region of the body cavity may be utilized to generate an aggregate diagnostic profile corresponding to the body cavity.

A method is also contemplated whereby the rigid elongate member of the enhanced dilatation device remains inserted or is re-inserted within the patient's body cavity in a substantially similar spatial orientation as in the diagnostic sequence, with the control unit may be operative to control the operation of at least one of the pumps to perform a treatment methodology derived from at least the aggregate diagnostic profile corresponding to the body cavity. The treatment methodology may comprise the transitioning of at least one of the plurality of inflation lumens to the inflated configuration, such that targeted dilatation is delivered to at least one of the diagnostic regions of the patient's body cavity. The treatment methodology may also comprise one or more of: the transitioning of a particular selected one or more of the inflation lumens to the inflated configuration, the transitioning of one or more inflation lumens to the inflated configuration so as to achieve a predefined particular measurement at the one or more pressure sensors associated with those inflation lumen, the transitioning of one or more inflation lumens between the inflated configuration and the deflated configuration a particular number of times over a particular time period, the transitioning of an inflation lumen to the inflated configuration or to the deflated configuration over a particular rate of time; or combinations thereof.

A diagnostic device for characterizing a patient's body cavity is also contemplated to comprise a rigid elongated member having a proximal end and a distal end, one or more emitters within the rigid elongate member operative to emit energy, and one or more sensors within the rigid elongate member operative to detect the effects of the energy emitted by the one or more emitters. The diagnostic device may be operative to perform a diagnostic sequence for characterizing a patient's body cavity into which the rigid elongate member is inserted, with the diagnostic sequence comprising at least one emitter emitting energy towards at least one diagnostic region of the body cavity, at least one of the sensors detecting the effects of the energy emitted towards the at least one diagnostic region of the body cavity by the at least one emitter, and determining a regional diagnostic status for each of the at least one diagnostic region of the body cavity based upon the detected effects. The emitters may be configured to emit one or more of an electromagnetic wave having a particular wavelength, an electromagnetic wave having a particular polarization; sonic energy having a particular frequency, sonic energy having a particular amplitude; or combinations thereof. The one or more emitters may comprise at least one emitter configured to transit along a longitudinal axis of the rigid elongate member between the proximal end and the distal end. The one or more emitters may comprise at least one emitter configured to rotate about a longitudinal axis of the rigid elongate member between the proximal end and the distal end. Each of the one or more determined regional diagnostic statuses for each of the one or more diagnostic regions of the body cavity may be utilized to generate an aggregate diagnostic profile corresponding to the body cavity.

Another method of administering targeting dilation therapy using the above diagnostic device may comprise the steps of providing a dilatation device comprising a rigid elongate member for insertion within the patient's body cavity according to a particular predefined spatial orientation derived from the diagnostic sequence performed by the diagnostic device, with the dilatation device being configured to perform a treatment methodology derived from at least the aggregate diagnostic profile corresponding to the patient's body cavity, and inserting the rigid elongate member into the patients' body cavity according to a particular predefined spatial orientation derived from the diagnostic sequence performed by the diagnostic device.

All of these embodiments are contemplated to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features and advantages of the various embodiments disclosed herein are better understood with respect to the following descriptions and drawings, in which.

Common reference numerals are used throughout the drawings and the detailed description to indicate the same elements.

DETAILED DESCRIPTION

Figure 1:
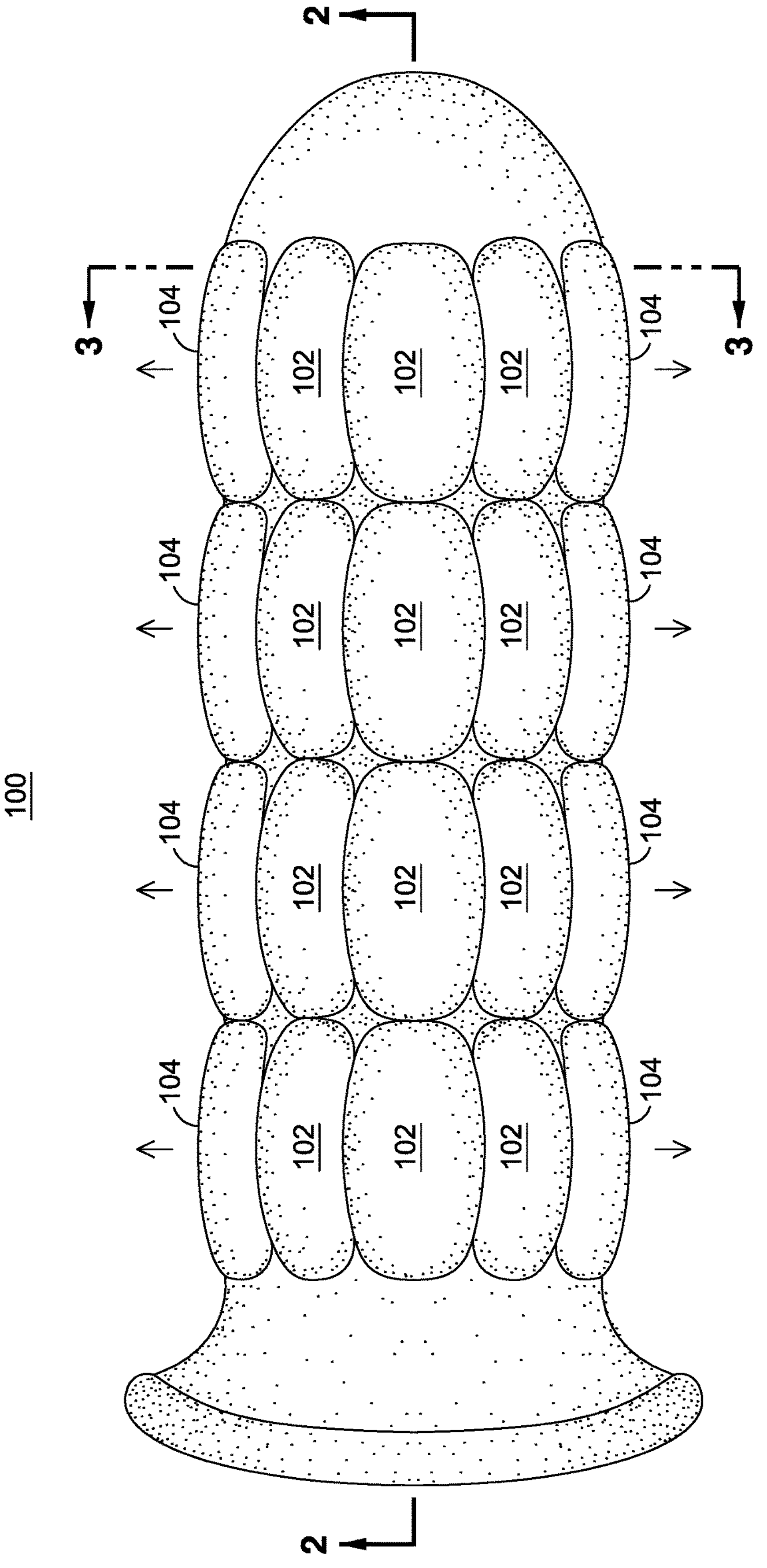
FIG. 1 is an elevation view of an enhanced dilation device according to a first exemplary embodiment of the present disclosure.

According to various aspects of the present disclosure, new and improved enhanced dilation devices for targeted diagnosis and targeted dilatation therapy are contemplated. The enhanced dilation device may comprise a rigid elongated member defining a longitudinal axis defining a proximal end, distal end, and a shaft region therebetween, with a sheath secured to and at least partially enclosing at least a portion of an exterior of the shaft region. A tubular inflatable balloon may act as the sheath to be placed around the shaft of a conventional rigid device, such as a dildo, a dilator, or a pelvic floor relaxer, for insertion into the body cavity of a patient or user including the vagina or anus. It is also contemplated that the enhanced device may be configured to be used or inserted into other areas of a user, such as blood vessels and the esophagus for use in angioplasty after atherectomy. The tubular balloon may define therein a plurality of internal lumens. A reservoir may be included inside the body of the device and filled with helium gas or another suitable fluid for inflating the balloon, in which said fluid could be referred to as an inflation fluid. A plurality of pumps may be associated with a plurality of inflation fluid pathways, defined by a plurality of conduits, between the reservoir and each of the plurality of inflation lumens.

The design may be configured such that each inflation lumen has a particular inflation fluid pathway with a particular pump. The plurality of pumps may function to inflate and deflate one or more of the inflation lumens via pumping the inflation fluid into or out of the one or more of the inflation lumens. Each one of the inflation lumens of the plurality of inflation lumens may be transitionable between at least an inflated configuration and a deflated configuration. When in the inflated configuration, a particular inflation lumen may be operative to cause a corresponding inflation portion of the outer surface of the balloon to expand outward, while in the deflated configuration, a particular inflation lumen may be operative to cause the corresponding inflation portion of the outer surface of the balloon to retract inwards. A plurality of pressure sensors may be associated with each of the inflation lumens to measure the pressure inside of the inflation lumens.

The plurality of inflation lumens may be operative to administer a specific dilation effect and/or treatment to be administered when one or more of the lumens are inflated to the inflated configuration. The treatment to be administered may include a therapeutic methodology or sexual stimulation. Due to the configuration of the device, control mechanisms may be implemented to enable the automatic or manual inflation and deflation of the plurality of inflation lumens via controlling the operation of one or more of the pumps. The control mechanisms may allow for selective inflation/deflation of one or more particular inflation lumens via controlling the operation of particular pumps. The pressure readings from one or more of the plurality of pressure sensors may be received by the control mechanisms.

The plurality of inflation lumens are separate from one another and as such the inflation fluid contained within a particular inflation lumen would not be able to travel directly into or leak directly into another inflation lumen, even if the inflation lumens are adjacent to each other. This allows for certain inflation lumens to contain more or less inflation fluid than others, which may allow for each inflation lumen to expand outwards to a unique degree. Thus, in some embodiments the plurality of inflation lumens may be operative to transition in between a spectrum of inflation configurations between the deflated configuration and the inflated configuration, which may depend on the amount of inflation fluid that has been pumped inside the inflation lumens. The degree to which each of the inflation lumens are inflated to may determine the expansion/retraction of the inflation portions corresponding to each particular inflation lumen.

The control mechanisms of the enhanced dilation device may be provided information to determine the degree at which to inflate each individual one of the plurality of inflation lumens. For example, each of the plurality of inflation lumens may be inflated such that each pressure sensor reads a specified pressure reading.

The plurality of inflation lumens need not be identical to one another, so the inflation lumens may be of differing sizes and shapes. Using different inflation lumens throughout the device may cause the inflation lumens to inflate and deflate differently from one another, require different amounts of inflation fluid to be pumped inside of them before reaching the inflated configuration, requiring different amounts of inflation fluid to be pumped outside of them before reaching the deflated configuration, and having entirely unique inflated configurations and deflated configurations from one another (for example, having two inflation lumens in the inflated configuration but with one being half the size and having a quarter of the volume of inflation fluid inside as the other inflation lumen). It can be seen that one or more of the inflation lumens of particular enhanced dilation devices may be shaped and sized as to target one or more particular diagnostic regions of a body cavity.

The ability of each individual one of the plurality of inflation lumens to be selectively inflated from the deflated configuration to the inflated configuration, and optionally inflation configurations in between those two, allow for a unique and novel treatment to be administered to the body cavity of a patient or user. The device may be inserted into a body cavity of a patient, and one or more of the plurality of inflation lumens may be operative to expand their corresponding inflation portion(s) against a respective corresponding diagnostic region(s) of the body cavity. If the inflation lumens are inflatable between a spectrum of inflation configurations, one or more particular inflation lumens may be inflated or deflated to a certain degree to allow for a certain level of pressure to be imparted and/or a dilation effect to be administered to one or more particular diagnostic regions. It can be seen that a unique dilation effect or treatment methodology may be administered and readily adjusted by expanding or retracting certain inflation portions of the sheath. The control mechanisms may utilize one or more pressure readings from the plurality of sensors to bring one or more of the inflation lumens to the proper inflation configuration.

A diagnostic sequence may be performed by the enhanced dilation device by determining one or more regional diagnostic statuses corresponding to the one or more diagnostic regions of the body cavity. The regional diagnostic status(es) may be determined by one or more pressure measurements from one or more of the plurality of pressure sensors and/or a measurement of the net flow of inflation fluid to or from one or more inflation lumens. The regional diagnostic status(es) may also be determined by a scanner, which will be discussed later in the disclosure herein. The diagnostic statuses may provide information about the corresponding diagnostic regions of the cavity, such as muscle strength, muscle condition, nerve density, nerve stretching diagnostic regional imaging or mapping, response of the diagnostic region to pressure applied to it by the corresponding inflation portion, etc. . . . These regional diagnostic statuses may be complied together to form an aggregate diagnostic profile for the body cavity.

This aggregate diagnostic profile may be read and used by the control unit to operate the pumps in order to perform a specialized treatment methodology for that body cavity. The enhanced dilation device may either remain in inserted in the body cavity or it may be re-inserted into the body cavity of a patient in substantially the same spatial orientation as in the diagnostic sequence to ensure the treatment methodology is performed correctly. The treatment methodology may comprise the transition of one or more of the inflation lumens to the inflated configuration such that a targeted dilation effect is delivered to at least one of the diagnostic regions of the body cavity. The treatment methodologies may further comprise a time based inflation/deflation of the inflation lumens, such as a rate of inflation, a cycling between configurations multiple times, a sudden or gradual inflation/deflation of one or more inflation lumens, etc. For example, if a particular diagnostic region is injured or bruised, a treatment methodology may comprise inflating the inflation lumens corresponding to the diagnostic regions surrounding this particular injured diagnostic region to the inflated configuration and keeping the inflation lumen corresponding to this particular diagnostic region at the deflated configuration. Another example of a treatment methodology is slowly inflating the inflation lumen corresponding to an injured diagnostic region over time to a desired inflation configuration so as to avoid a sudden reaction that could be caused by quickly applying pressure to that diagnostic region. The inflation and deflation of the plurality of inflation lumens, along with the operation of ancillary features such as vibrators, may also be operative to administer a grinding effect on one or more the diagnostic regions.

The enhanced dilation device may further comprise a scanner which may itself comprise one or more emitters operative to emit energy as well as one or more sensors operative detect the effects of the energy emitted by those one or more emitters. The emitters and sensors may scan, diagnose, detect, and/or measure one or more conditions on the diagnostic regions, such as condition of a muscle (soreness, bruises, tears, etc.) to solely form or to be used in combination with other data (such as the aforementioned one or more pressure readings from the pressure sensors) to form one or more regional diagnostic statuses. This may be done via at least one sensor detecting the effects of the energy emitted by the emitters towards one or more of the diagnostic regions of the body cavity of a patient or user. The emitters and scanners may also be operative to image the body cavity the enhanced dilation device is inserted into. This image may be analyzed by the scanner or through other means to provide more information on the regional diagnostic statuses. This information may include, for example, the density of nerves in a certain area or the stretching of nerves in particular directions, which could prove useful in determining the proper treatment methodology to treat the body cavity.

The scanner and its emitters and sensors may further be operative to scan the diagnostic regions to measure compositions and presence of certain species on or within the diagnostic regions. For example, the scanner may detect the presence and/or amount of calcium in vessels corresponding to the diagnostic regions, and a treatment methodology may comprise operating the enhanced dilation device so as to administer a grinding effect to dislodge this undesired calcium buildup. This information could also be used to determine the presence/amount of calcium on the outside of vessels, which could then be utilized to treat the calcium buildup through other means such as by applying an ultrasonic frequency.

The device may be configured such that each emitter corresponds to a particular diagnostic region or that one or more of the emitters may correspond to more than one diagnostic region. In the latter case, the one or more emitters may be operative to move relative to the enhanced dilation device and/or the scanner to emit energy towards more than one diagnostic region. In this case, the sensors may be operative to determine which detected emitted energy effect corresponds to which diagnostic region, which could be via the positioning of the sensors corresponding to which emitted energy they detect. The emitters can come in various forms, such as cameras, electromagnetic wave emitters, sonic wave emitters, a radiofrequency emitter, a laser emitter, an electrical stimulation emitter, and combinations thereof. This data may be fed to a control unit to form an aggregate diagnostic profile, which may then be used by the control unit to selectively inflate/deflate a plurality of inflation lumens via operation of one or more pumps to treat the one or more diagnostic regions.

The enhanced dilation device may serve instead as a diagnostic device that serves mainly to house the one or more emitters and one or more sensors such that they may generate one or more regional diagnostic statuses of the diagnostic regions one inserted into the body cavity. For this type of diagnostic device, features that contribute to administering a dilation effect or treatment, such as the plurality of inflation lumens, may be omitted. The regional diagnostic statuses or an aggregate diagnostic profile generated from the diagnostic statues may be used to make or configure a dilation device which may be especially suitable for performing a treatment methodology intended for a particular body cavity. This may allow for a very personalized treatment methodology to be given to a patient or user that pertains to them and any conditions they may have, which allows for much greater results than what could be obtained from prior art methods.

Any of the enhanced dilation devices discussed herein may incorporate features of Applicant's previous applications, specifically U.S. patent application Ser. No. 17/655,761, entitled IMPROVED DILATATION DEVICE INCORPORATING INFLATABLE BALLOON, Applicant's prior filed U.S. patent application Ser. No. 17/646,309 entitled ENHANCED PROPHYLACTICS FOR VACUUM THERAPY, Applicant's prior filed U.S. patent application Ser. No. 17/809,357 entitled IMPROVED DILATATION DEVICES INCORPORATING ENHANCED FEATURES, and Applicant's prior filed U.S. patent application Ser. No. 17/931,411 entitled RESILIENT ADHESIVE SHEATH FOR USE WITH DILATION DEVICE, with the entire disclosure of each being incorporated herein as if fully restated.

Turning now to FIG. 1, an elevation view of an enhanced dilation device according to a first exemplary embodiment of the present disclosure is shown. An enhanced dilation device 100 is provided with a plurality of inflation lumens 102 along with their corresponding inflation portions. In the illustrated embodiment, it may be seen that the array of inflation lumens 102 are arrayed about the exterior of the shaft portion of the rigid elongate member, with twenty pictured and a total of thirty-two in the specific device shown (twelve not shown). However, according to other embodiments, there can be more or fewer inflation lumens 102, along the horizontal axis or anywhere else throughout the enhanced dilation device 100. The plurality of inflation lumens 102 are depicted here in an orderly array, but in differing embodiments they can be arranged in disorderly configuration and/or abstract arrangements. The plurality of inflation lumens 102 may be seen to be operative to expand, with each having a corresponding outer surface 104 expanding outward and away from the enhanced dilation device 100, This outward expansion may be operative to cause the outer surfaces 104 to apply a pressure against the external surfaces against which they are contacted, such as the diagnostic regions of the body cavity.

The enhanced dilation device 100 may also be configured such that each of the plurality of inflation lumens 102 may be configured differently from one another, such that their respective corresponding outer surfaces 104 outwardly expand in different ways. For example, a particular inflation lumen 102 may be at the inflated configuration in which the particular corresponding outer surface 104 expands outwards to a substantial degree, while another inflation lumen 102 may be configured such that its outer surface 104 to an intermediate degree when expanded to the inflated configuration, while a further inflation lumen 102 may be configured to have an outer surface 104 which expand outwards to a reduced degree when transitioned to the inflated configuration. Likewise, it may be seen that the transition between the expanded and deflated configurations may be a matter of degree, and it may be possible to partially transition between maximal and minimal expansion, or to expand with a greater resilience, and that such expansion may also be resisted by the presence of external resilient surfaces for which the level of resilience may differ, and that such, the degree to which any given inflation lumen 102 is transitioned to the inflated configuration may be relative to the circumstances in which it is placed in, and that such transition may further occur under circumstances in which a more or less compressible fluid is used to pressurize the inflation lumen to cause such an expansion. Likewise, it may be seen that an inflation lumen 102 is inflated with a compressible fluid (such as a gas), if placed under an external pressure, the lumen itself may be reduced in volume. In this fashion, it may be seen that the concepts of any inflation lumen 102 being transitioned to or from the expanded or default configurations is relative and is not to be interpreted as a change in any particularly defined internal volume of the inflation lumen 102, but rather is to be understood as referring to the relative act of actively pumping inflation fluid in or out of the inflation lumen and to or from the reservoir via action of the pumps according to the present disclosure. In this way, it may be seen that an inflation lumen 102 may, for example, be transitioned to the inflated configuration even if its internal volume does not substantially change (e.g. via a net flow of a compressible inflation fluid into the inflation lumen 102 under external pressure which results in an increase in pressure but not of volume). It may also be seen that the inflation lumen may be said to be transitioned to the deflated configuration by any net action of the corresponding pump to remove inflation fluid from the inflation lumen. It may further be seen that an inflation lumen 102 need not be fully inflated or deflated to be in the inflated or deflated configuration, and that such language refers to the most recent relative net change of the inflation fluid within that particular lumen via action of the pumps, such that, for example, that a lumen that was recently transitioned "to the inflated configuration" may still have less inflation fluid present therein than a different lumen that was recently transitioned "to the deflated configuration."

The enhanced dilation device 100 illustrated in FIG. 1 has a generally linear ovoid shape, similar to many conventional dilator or dildo products currently offered for sale. It may be seen, however, that the shape, size, and exterior features of the enhanced dilation device in any embodiment may be substantially varied or customized, similar to the way that many conventional dilator or dildo products are also varied, including in size, shape, curvature, color, etc. It is also contemplated that the plurality of inflation lumens in any embodiment may be shaped and configured in various different ways, and that each inflation lumen on a particular enhanced dilation device need not be of the same shape, size, or configuration. For instance, one inflation lumen may be larger than another inflation lumen positioned next to each other, which would allow for the larger inflation lumen to expand against a larger diagnostic region of the body cavity. As such, it can be seen that different types of inflation lumens will inflate differently and therefore expand a different sized inflation portions against the diagnostic regions in a different manner, even if a similar amount of inflation fluid has been pumped inside of a particular set of inflation lumens 102.

Figure 2:
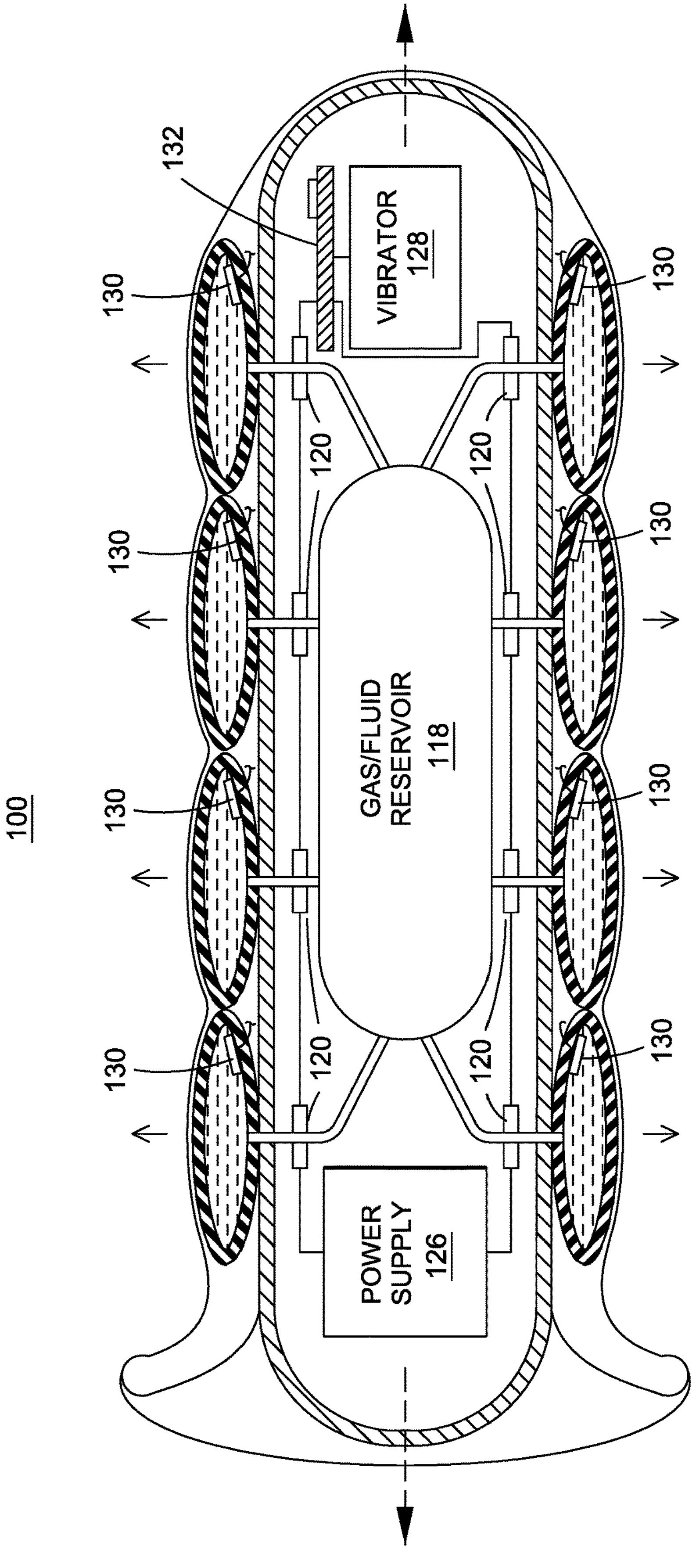
FIG. 2 is a side cutaway view along line 2 in FIG. 1 of the enhanced dilation device according to the first exemplary embodiment of the present disclosure.

Turning now to FIG. 2, a side cutaway view along line 2 of FIG. 1 of the enhanced dilation device according to the first exemplary embodiment of the present disclosure is shown. The plurality of inflation lumens 102 of the enhanced dilation device 100 may contain an inflation fluid that is pumped to and from a reservoir 118. Inflation fluid may be pumped into and out of the plurality of inflation lumens 102 to transition the plurality of inflation lumens 102 to spectrum of inflated and deflated configurations. A plurality of pumps 120, which may take the form of bi-directional pumps, positioned on a plurality of inflation fluid pathways 122 are operative to pump the inflation fluid from the inflation fluid reservoir 118 to and from the plurality of inflation lumens 102. The plurality of inflation fluid pathways 122 are depicted here to be of equal size and shape, but it is contemplated that the plurality of inflation fluid pathways 122 may be configured differently from one another, such as having a larger cross section or having a varying shape throughout the inflation fluid pathway 122.

Additionally, while each of the plurality of inflation fluid pathways 122 are depicted here to correspond to one particular inflation lumen 102, it is contemplated that in separate embodiments two or more inflation fluid pathways 122 may converge into a particular inflation lumen 102 or that an inflation fluid pathway 122 may diverge into two or more inflation fluid pathways 122 each leading to a different inflation lumen 102. In these types of embodiments, a pump 120 may be placed on the inflation fluid pathway 122 ahead of or behind the point wherein the inflation fluid pathway 122 converges or diverges, which may allow for a particular pump 120 to pump inflation fluid to or from two or more inflation lumens 102. A control unit 132 may control the operation of the pumps 120, as well as other ancillary features such as the vibrator 128, and may receive pressure measurements from the pressure sensors 130 within the inflation lumens 102.

The plurality of pumps 120 may operate independently from one another, and as such some pumps 120 may pump inflation fluid to or from some the plurality of inflation lumens 102 while the other pumps 120 may be idle. A power supply 126 may be provided to power one or more of the plurality pumps 120 and any other additional features such as a vibrator 128. A plurality of pressure sensors 130 may be placed inside of the plurality of inflation lumens 102 which may measure the pressure inside a particular inflation lumen 102.

Figure 3:
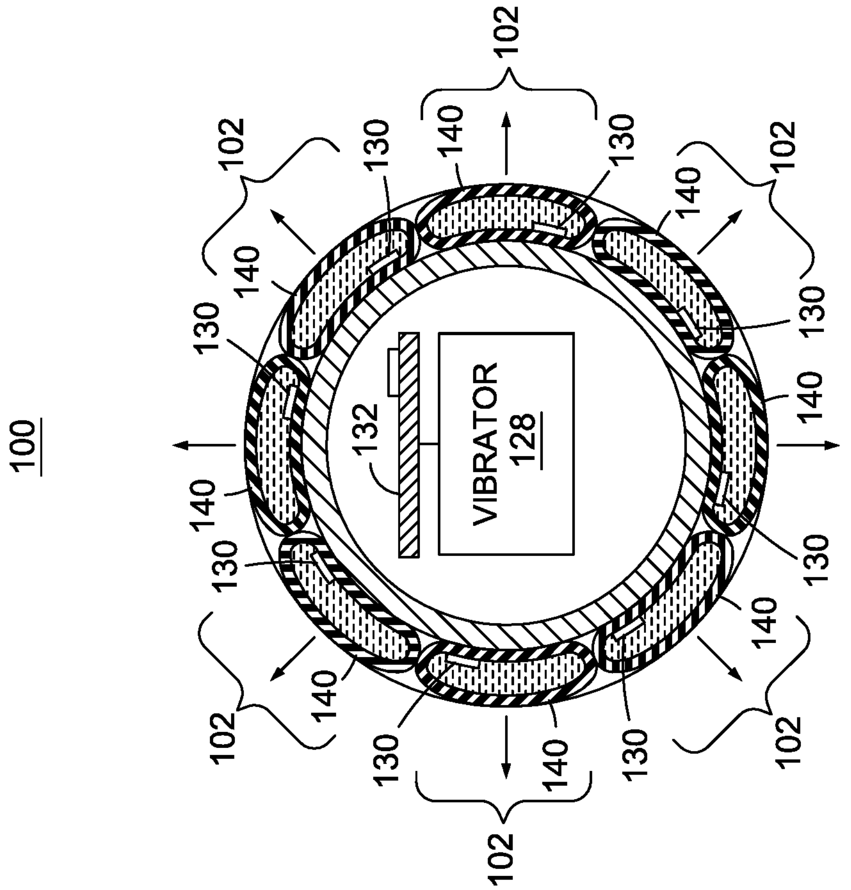
FIG. 3 is a front cutaway view along line 3 in FIG. 1 of the enhanced dilation device according to the first exemplary embodiment of the present disclosure.

Turning now to FIG. 3, a front cutaway view along line 3 in FIG. 1 of the enhanced dilation device according to the first exemplary embodiment of the present disclosure is shown. Here, it may be seen that the plurality of inflation lumens 102 completely surround the rigid elongate member of the enhanced dilation device 100. However, the plurality of inflation lumens 102 need not completely surround the shaft region of the enhanced dilation device 100 has shown here. In this embodiment of the enhanced dilation device 100, it can be seen that each of the plurality of inflation lumens 102 may expand outward in different directions, which may be taken advantage of by this particular embodiment of an enhanced dilation device 100 to cause outer surfaces 104 to expand against most of the available diagnostic regions of the body cavity. Depending on the level of inflation/deflation of the plurality of inflation lumens 102, it can be seen that a different outward expansion effect which may be operative to, for example, administer a different dilation effect be delivered each outer surfaces 104 of each of the plurality of inflation lumens 102, and accordingly, a different pressure measurement will result in each pressure sensor 130 within each of the inflation lumens 102 according to the resilience of the diagnostic region corresponding to that inflation lumen 102, with a more resilient diagnostic region resulting in a greater pressure being measured within the inflation lumen 102 for a given amount of inflation fluid being pumped therein, and a lesser pressure being measured for a less resilient diagnostic region. In this fashion, it may be seen that by, for example, inserting an enhanced dilatation device 100 into a patient's orifice and thereafter inflating a plurality of substantially identical inflation lumens 102 with a predetermined amount of inflation fluid and by measuring the differences in pressure readings on the respective pressure sensors 130 resulting therefrom, the differences in the resilience of the various diagnostic regions of the patient's orifice may be determined.

Figure 4:
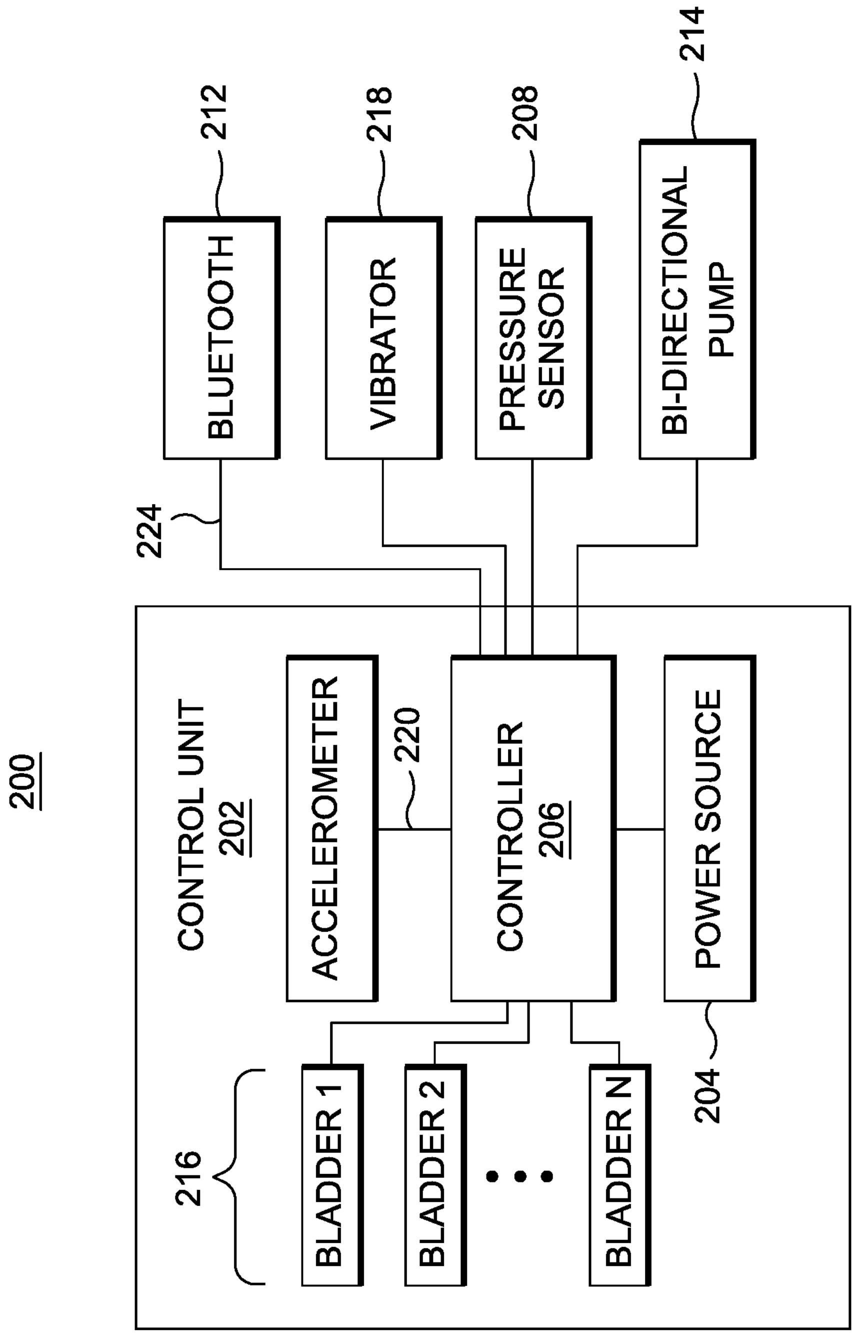
FIG. 4 illustrates an exemplary block diagram of a control unit according to a second exemplary embodiment of the present disclosure.

Turning now to FIG. 4, an exemplary block diagram of a control unit according to a second exemplary embodiment of the present disclosure is shown. The block diagram 200 represents the interconnections 220 and intraconnections 224 of the control unit 202. Each of the interconnections 220 and intraconnections 224 may be via direct wiring or via a wireless connection. A power source 204 may provide power to at least a controller 206. The controller 206 may be operative to receive information from other devices, such as one or more pressure sensors 208 operative to measure the pressure inside one or more inflation lumens and/or an accelerometer 210 operative to measure the direction and the velocity of the enhanced dilation device's travel. This information can be used to form one or more regional diagnostic statuses and the aggregate diagnostic status. The controller 206 may then use the information from these sensors and/or information from a user via a Bluetooth® sensor 212, for instance, to control the operation of one or more bi-directional pumps 214 to inflate/deflate one or more inflation lumens 216. The controller 206 may further be operative to transmit information to a user via the aforementioned Bluetooth® sensor 212; this information can include the readings from the one or more pressure sensors, one or more of the regional diagnostic statuses, the aggregate diagnostic status, etc. The controller 206 may be further operative to control the operation of additional features such as one or more vibrators 218.

Figure 5:
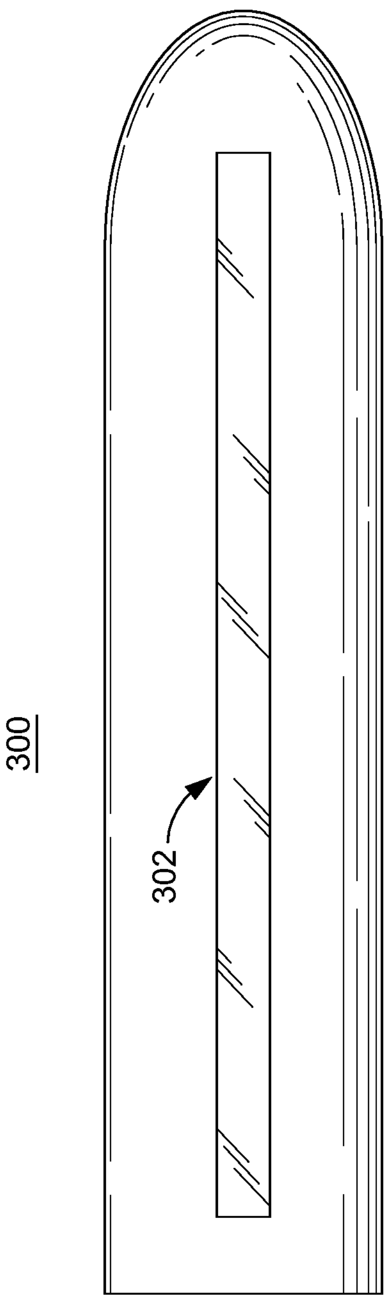
FIG. 5 is an elevation view of an enhanced dilation device according to a third exemplary embodiment of the present disclosure.

Turning now to FIG. 5, an elevation view of an enhanced dilation device according to a third exemplary embodiment of the present disclosure is illustrated. In this enhanced dilation device 300, a scanner 302 is embedded inside the enhanced dilation device 300. The scanner 302 comprises one or more emitters (not depicted) operative to emit energy and one or more sensors (not depicted) operative to detect the effects of energy emitted by the one or more emitters. The illustration here omits features shown in the previous figures, such as the inflation lumens, the pumps, the inflation lumens, etc., and those features may or may not be included in an embodiment which has the scanner 302. It may also be seen that the enhanced dilation device 300 may only serve as a housing for the scanner 302 so that the enhanced dilation device 300 may be used as an insertable diagnostic device that may scan, detect, diagnose, image and/or measure the diagnostic regions as opposed to a device that may be further operative to administer treatment to those diagnostic regions.

Figure 6:
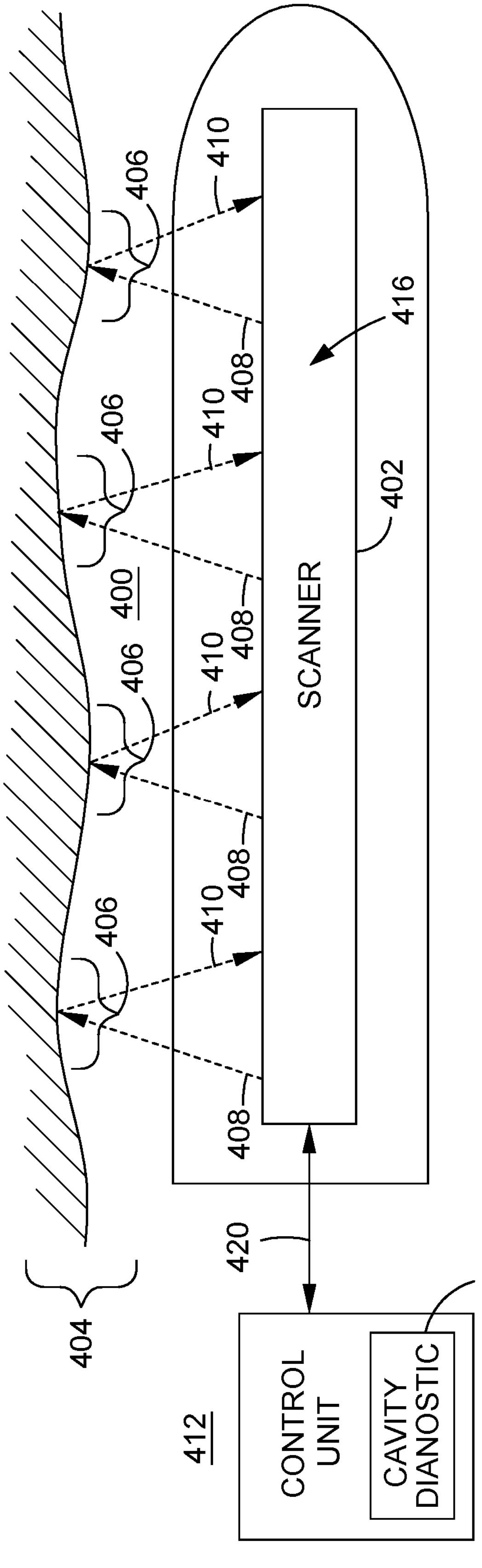
FIG. 6 is an elevation view of an enhanced dilation device according to a fourth exemplary embodiment of the present disclosure being used within a cavity.

Turning now to FIG. 6, an elevation view of an enhanced dilation device according to a fourth exemplary embodiment of the present disclosure is shown being used within a patient's cavity. This enhanced dilation device 400, which comprises a scanner 402, has been inserted into the body cavity 404 of a user with multiple diagnostic regions 406. One or more of the emitters (not explicitly shown) of the scanner 402 may emit energy 408 that originates from the emitter of the scanner 402 and is sent towards a diagnostic region 406 of the body cavity 404. The emitted energy 408 may then result in an effect 410 which may then be received or detected by one or more sensors (not explicitly shown) of the scanner 402. This effect may then be analyzed to derive data in order to determine the regional diagnostic status for a particular diagnostic region 406. The one or more emitters of the scanner 402 may comprise, but are not limited to, cameras, electromagnetic wave emitters, a radiofrequency emitter, a laser emitter, an electrical stimulation emitter, a sonic energy emitter, or combinations thereof. The sensor of the scanner 402 may comprise any sensor operative to determine the regional diagnostic status for the diagnostic regions 406 by detecting the effect 410 of the energy 408 given off by the emitters. It is to be understood that the scanner 402 and its sensors and emitters may comprise other scanning devices not explicitly stated herein, including scanners that have not yet been discovered or conceived of, that are suitable and operative to determine the regional diagnostic status of at least one diagnostic region 406. Conditions that the scanner 402 may measure to determine the regional diagnostic statuses include, but are not limited to, damaged muscle, torn muscle, muscle mapping, diagnostic regional imaging and combination thereof.

As can be seen in FIG. 6, the site at which the energy 408 is emitted by the emitter and the site at which the effect 410 is sensed by the sensor may be spaced from each other, and as such it may be further seen that the scanner 402 may be configured such that the positioning of the sensors are operative to detect the effect 410 from a particular emitter corresponding to a particular diagnostic region 406. The sensor or other features of the scanner 402 may be operative to identify which diagnostic region 406 corresponds to the regional diagnostic status determined by the sensor, which could be necessary in a device such as the one depicted in FIG. 6 where the sensors and emitters are offset from their respective diagnostic regions.

Additionally, the emitters may be configured such that the emitter(s) may move relative to the scanner 402 and/or the enhanced dilation device 400 to scan multiple diagnostic regions 406. The emitter may transit along a longitudinal axis of the enhanced dilation device 400 and/or the scanner 402, and/or it may rotate about that same longitudinal axis. This way the emitter may scan the diagnostic regions 406 of the body cavity 404 similar in manner to how a scanner in a printer may scan a page. In this embodiment, multiple sensors may be operative to detect the effect 410 of energy 408 emitted by one of the one or more emitters, or a single sensor and a single emitter may be used to scan the entire surface of the patient's orifice, if it is able to both move longitudinally and rotationally.

A control unit 412 may be included which can control the operation of the emitters and sensors of the scanner 402. The control unit 412 may further be operative to receive and read data gathered by the scanner 402 through a communication link 420 to make a cavity diagnostic 414 that may act as one or more regional diagnostic statuses or the aggregate diagnostic status. The cavity diagnostic 414 may comprise the raw data gathered by the sensors of the scanner 402 or it may comprise a form of data that has been processed into a format that can be used to more readily diagnose or measure the one or more regional diagnostic statuses. A plurality of inflation lumens are omitted from this embodiment, but if they were included the control unit 412 may be further operative to use the cavity diagnostic 414 to control the inflation/deflation of the plurality of inflation lumens in order to administer a treatment methodology specific to that cavity diagnostic 414. The control unit 412 may accomplish this through a communication 420 with, for example, a plurality pumps operative to pump an inflation fluid into and out of the plurality of inflation lumens to expand them against the diagnostic regions 406.

The enhanced dilation device 400 may further comprise a scanner friendly material 416 which is operative to allow for the emitted energy 408 and/or the effect 410 to travel through the enhanced dilation device 400 so the one or more regional diagnostic statuses may be determined without interfering with the emitted energy 408 and/or the effect 410, which if not done could otherwise lead to false regional diagnostic statuses being determined. Depending on the scanner 402 being used and the emitter(s) and sensor(s) found on them, a particular scanner friendly material 416 may be chosen for the most accurate results, as would be understood by those skilled in the art. In some embodiments, the plurality of inflation lumens may be made of this scanner friendly material 416; the emitter(s) of the scanner 402 may emit energy 408 and the sensor(s) may detect the resultant effect 410 through the scanner friendly material 416 of the inflation lumens. In this case, the control unit 412 may be able to administer the treatment methodology by determining the regional diagnostic statuses of one or more diagnostic regions 406 of the body cavity 404 and then subsequently inflating/deflating the inflation lumen(s) corresponding to the diagnostic region(s) 406.

Figure 7:
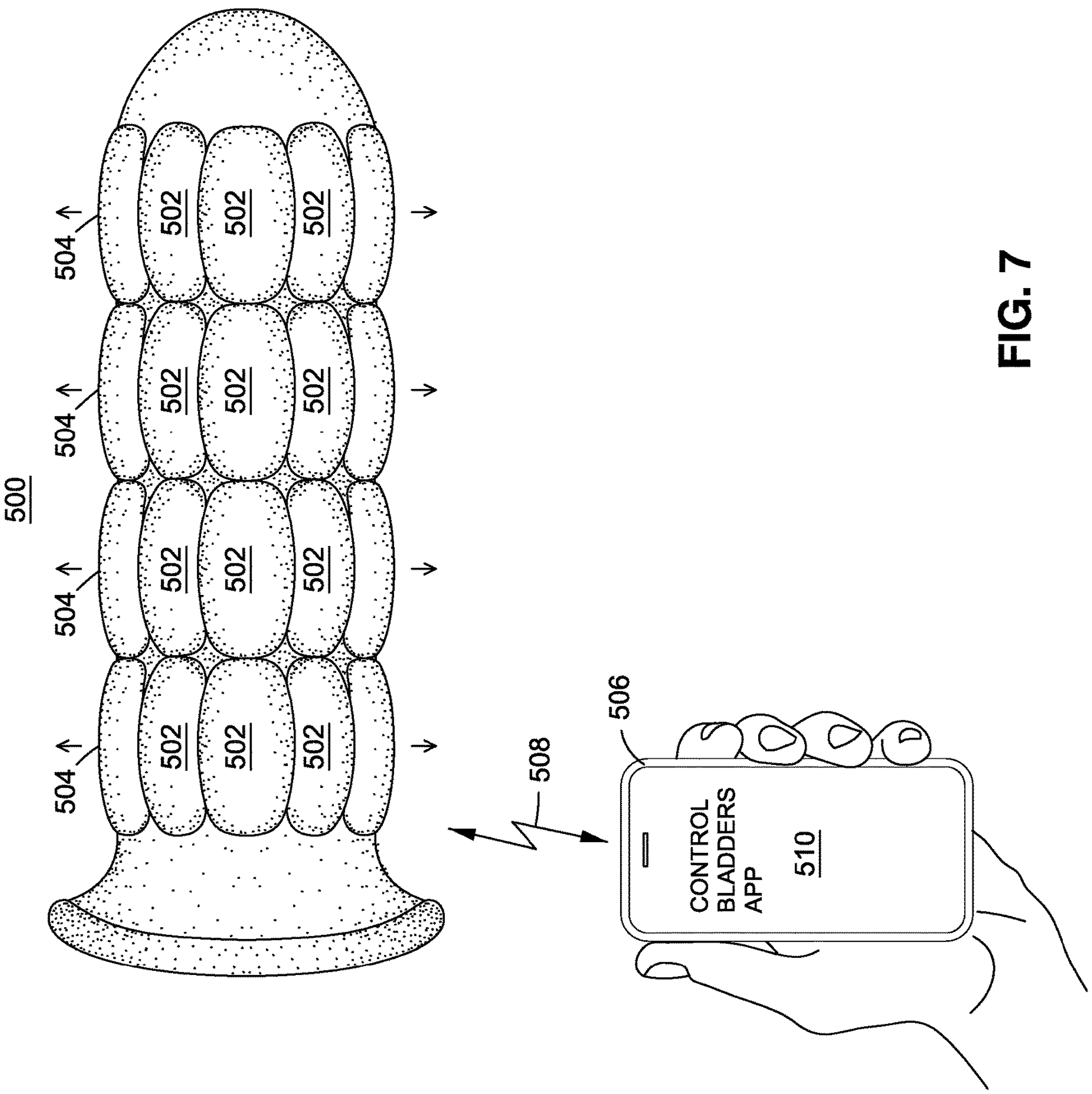
FIG. 7 is an elevation view of an enhanced dilation device according to a fifth exemplary embodiment of the present disclosure along being controlled by a mobile device.

Turning now to FIG. 7, an elevation view of an enhanced dilation device according to a fifth exemplary embodiment of the present disclosure along being controlled by a mobile device is depicted. Here, an enhanced dilation device 500 has a plurality of inflation lumens 502 being operative to enable their outer surfaces 504 to expand outward and away from the enhanced dilation device 500. This enhanced dilation device 500 would contain a controller (not explicitly depicted) which may be operative to control inflation/deflation of the plurality of inflation lumens 502 and thus the level and/or force of outward expansion. In this embodiment, a mobile device 506 is in communication 508 with the control unit. This communication 508 may be done via the aforementioned Bluetooth® connection, for example. The mobile device 506 may be made specifically to communicate with and control the functions of the control unit, or it may be a device that serves several other purposes, such as a smartphone, with a software app 510 residing onto it enable it to communicate with a transceiver on the rigid elongate member, which either with a control unit within the rigid elongate member, or in certain embodiments functioning as the control unit itself, either standing alone or in combination with another portion of the control unit within the rigid elongate member of the enhanced dilatation device 500. The mobile device 506 may also be replaced with some other electronic device such as a personal computer or a medical device, as would be appreciated by those skilled in the art. The mobile device 506 may allow a user to selectively choose which of the plurality of inflation lumens 502 to inflate/deflate and to what degree the plurality of inflation lumens 502 will be inflated/deflated via communication 508 with the control unit. The mobile device 506 may also allow a user to review one or more of a regional diagnostic status, an aggregate diagnostic profile or generated treatment methodology. The mobile device 506 may also allow a user to select or generate or edit a particular treatment methodology, or to trigger the performance of a diagnostic sequence or the performance of a treatment methodology.

Additionally, one or more treatment methodology profiles may be programmed into the mobile device 506 and/or app 510 which the user may select and have the control unit automatically inflate/deflate each of the plurality of inflation lumens 502 to the configuration dictated by that particular treatment methodology profile. The user may change between different inflation profiles while the enhanced dilation device 500 is inside the body cavity, such that the user may change from one treatment methodology to the next when desired. The mobile device 506 may be further operative to receive information gathered from one or more of the types of sensors in communication with the control unit, allowing a user to monitor the operation of the enhanced dilation device 500 or collect and report data from the sensors. The aforementioned diagnostic profile, comprising one or more regional diagnostic statuses or the aggregate diagnostic status, may be collected and reported via the mobile device 506, with the mobile device 506 being further operative to send and share this data with other devices.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combinations with each other and are not intended to be limited to the specific combination disclosed herein. Thus, the scope of the claims is not to be limited by the illustrated embodiments. Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. An enhanced dilatation device for targeted dilatation therapy, the enhanced dilatation device comprising:

a rigid elongated member having a proximal end, a distal end, and a shaft region therebetween;

a sheath secured to and at least partially enclosing at least a portion of an exterior of the shaft region, the sheath having an outer surface and a plurality of inflation lumens, each individual one of the plurality of inflation lumens being transitionable between at least a deflated configuration and an inflated configuration, wherein transitioning of each individual inflation lumen to the inflated configuration is operative to cause a respective inflation portion of the outer surface corresponding to that inflation lumen to expand away from the exterior of the shaft region, and wherein transitioning of each individual inflation lumen to the deflated configuration is operative to cause that respective inflation portion of the outer surface corresponding to that inflation lumen to retract towards the exterior of the shaft region;

a reservoir operative to contain inflation fluid;

a plurality of conduits defining respective inflation fluid pathways between the reservoir and each respective inflation lumen;

a plurality of pumps, at least one pump being associated with each inflation fluid pathway, each at least one pump being operative to regulate the net flow of inflation fluid between the reservoir and a respective inflation lumen along the respective inflation fluid pathway, a net flow of inflation fluid from the reservoir into a respective inflation lumen being associated with the transition of that inflation lumen to the inflated configuration, and a net flow of inflation fluid from the respective inflation lumen into the reservoir being associated with the transition of that inflation lumen to the deflated configuration;

a plurality of pressure sensors, each respective one of the inflation lumens having associated therewith at least one respective pressure sensor for measuring the pressure within that inflation lumen; and a control unit operative to control at least the operation of the plurality of pumps and to receive measurements from the plurality of pressure sensors; and wherein each of the plurality of lumens are configured to be selectively inflated and deflated between a spectrum of inflation configurations independent of each other lumen.

2. The enhanced dilatation device of claim 1, wherein the enhanced dilatation device is operative to perform a diagnostic sequence for characterizing a patient's body cavity into which the rigid elongate member is inserted, the diagnostic sequence comprising one or more of the plurality of inflation lumens being transitioned to the inflated configuration such that each respective inflation portion of the outer surface corresponding to those one or more inflation lumens expands against a respective corresponding diagnostic region of the body cavity and each at least one pressure sensor associated with the one or more of the plurality of inflation lumens transitioned to the inflated configuration detects at least one pressure measurement within that inflation lumen, and based upon the at least one detected pressure measurement, a regional diagnostic status is determined for each diagnostic regions of the body cavity.

3. The enhanced dilatation device of claim 2, wherein at least one regional diagnostic status for at least one of the diagnostic regions of the body cavity is determined based upon a combination of the at least one detected pressure measurement within the one or more of the plurality of inflation lumens corresponding to that at least one diagnostic region, and the net flow of inflation fluid flowed to the one or more of the plurality of inflation lumens via the operation of the pump associated with the inflation fluid pathway between the one or more of the plurality of inflation lumens and the reservoir.

4. The enhanced dilatation device of claim 2, wherein each regional diagnostic status for each of the respective diagnostic regions of the body cavity is determined based upon a plurality of detected pressure measurements within the one or more of the plurality of inflation lumens corresponding to the diagnostic regions taken at different times during the transitioning of the one or more of the plurality of inflation lumen to the inflated configuration.

5. The enhanced dilatation device of claim 2, wherein each of the determined regional diagnostic statuses for each diagnostic region of the body cavity are utilized to generate an aggregate diagnostic profile corresponding to the body cavity.

6. The enhanced dilatation device of claim 5, wherein following the performance of the diagnostic sequence, the enhanced dilatation device is operative to administer treatment to the patient via the rigid elongate member remaining inserted or being re-inserted within the patient's body cavity in a substantially similar spatial orientation as in the diagnostic sequence, and the control unit being operative to control the operation of at least one of the pumps to perform a treatment methodology derived from at least the aggregate diagnostic profile corresponding to the body cavity, the treatment methodology comprising the transitioning of at least one of the plurality of inflation lumens to the inflated configuration, such that targeted dilatation is delivered to at least one of the diagnostic regions of the patient's body cavity.

7. The enhance dilation device of claim 6, wherein the treatment methodology comprises one or more of: the transitioning of a particular selected one or more of the inflation lumens to the inflated configuration; the transitioning of one or more inflation lumens to the inflated configuration so as to achieve a predefined particular measurement at the one or more pressure sensors associated with those inflation lumen; the transitioning of one or more inflation lumens between the inflated configuration and the deflated configuration a particular number of times over a particular time period; the transitioning of an inflation lumen to the inflated configuration or to the deflated configuration over a particular rate of time; or combinations thereof.

8. The enhanced dilatation device of claim 6, wherein following the performance of one or more treatment methodologies, the enhanced dilatation device is operative to repeat the performance of the diagnostic sequence in order to assess the results of the performance of the one or more treatment methodologies and to generate a new regional diagnostic status for each of the diagnostic regions of the body cavity, the repeat performance of the diagnostic sequence being performed via the rigid elongate member remaining inserted or being re-inserted within the patient's body cavity in a substantially similar spatial orientation as in the previous diagnostic sequence.

9. A method for performing a diagnostic sequence for characterizing a patient's body cavity, the method comprising the steps of:

providing an enhanced dilatation device, the enhanced dilatation device comprising:

a rigid elongated member having a proximal end, a distal end, and a shaft region therebetween;

a sheath secured to and at least partially enclosing at least a portion of an exterior of the shaft region, the sheath having an outer surface and a plurality of inflation lumens, each individual one of the plurality of inflation lumens being transitionable between at least a deflated configuration and an inflated configuration, wherein transitioning of each individual inflation lumen to the inflated configuration is operative to cause a respective inflation portion of the outer surface corresponding to that inflation lumen to expand away from the exterior of the shaft region, and wherein transitioning of each individual inflation lumen to the deflated configuration is operative to cause that respective inflation portion of the outer surface corresponding to that inflation lumen to retract towards the exterior of the shaft region;

a reservoir operative to contain inflation fluid;

a plurality of conduits defining respective inflation fluid pathways between the reservoir and each respective inflation lumen;

a plurality of pumps, at least one pump being associated with each inflation fluid pathway, each at least one pump being operative to regulate the net flow of inflation fluid between the reservoir and a respective inflation lumen along the respective inflation fluid pathway, a net flow of inflation fluid from the reservoir into a respective inflation lumen being associated with the transition of that inflation lumen to the inflated configuration, and a net flow of inflation fluid from the respective inflation lumen into the reservoir being associated with the transition of that inflation lumen to the deflated configuration a plurality of pressure sensors, each respective one of the inflation lumens having associated therewith at least one respective pressure sensor for measuring the pressure within that inflation lumen; and a control unit operative to control at least the operation of the plurality of pumps and to receive measurements from the plurality of pressure sensors;

inserting the rigid elongate member into the patient's body cavity and causing one or more of the plurality of inflation lumens to be transitioned to the inflated configuration such that each respective inflation portion of the outer surface corresponding to those one or more inflation lumens expands against a respective corresponding diagnostic region of the body cavity and each at least one pressure sensor associated with the one or more of the plurality of inflation lumens transitioned to the inflated configuration detects at least one pressure measurement within that inflation lumen; and;

determining, from the at least one detected pressure measurement, a regional diagnostic status for each diagnostic regions of the body cavity.

10. The method of claim 9, wherein at least one regional diagnostic status for at least one of the diagnostic regions of the body cavity is determined based upon a combination of the at least one detected pressure measurement within the inflation lumens corresponding to that at least one diagnostic region, and the net flow of inflation fluid flowed to that inflation lumen via the operation of the pump associated with the inflation fluid pathway between that inflation lumen and the reservoir.

11. The method of claim 9, wherein each regional diagnostic status for each of the respective diagnostic regions of the body cavity is determined based upon a plurality of detected pressure measurements within the inflation lumens corresponding to that diagnostic region taken at different times during the transitioning of that inflation lumen to the inflated configuration.

12. The method of claim 9, wherein each of the determined regional diagnostic statuses for each diagnostic region of the body cavity are utilized to generate an aggregate diagnostic profile corresponding to the body cavity.

13. A method of administering targeting dilatation therapy following the performance of the method of claim 12, the method comprising the rigid elongate member of the enhanced dilatation device remaining inserted or being re-inserted within the patient's body cavity in a substantially similar spatial orientation as in the diagnostic sequence, and the control unit being operative to control the operation of at least one of the pumps to perform a treatment methodology derived from at least the aggregate diagnostic profile corresponding to the body cavity, the treatment methodology comprising the transitioning of at least one of the plurality of inflation lumens to the inflated configuration, such that targeted dilatation is delivered to at least one of the diagnostic regions of the patient's body cavity.

14. The method of claim 13, wherein the treatment methodology comprises one or more of: the transitioning of a particular selected one or more of the inflation lumens to the inflated configuration; the transitioning of one or more inflation lumens to the inflated configuration so as to achieve a predefined particular measurement at the one or more pressure sensors associated with those inflation lumen; the transitioning of one or more inflation lumens between the inflated configuration and the deflated configuration a particular number of times over a particular time period; the transitioning of an inflation lumen to the inflated configuration or to the deflated configuration over a particular rate of time; or combinations thereof.

* * * * *